US011111473B2

(12) United States Patent
Van Hecke et al.

(10) Patent No.: US 11,111,473 B2
(45) Date of Patent: Sep. 7, 2021

(54) METHOD AND SYSTEM FOR PRODUCING PRODUCTS BY FERMENTATION

(71) Applicant: VITO NV (VLAAMSE INSTELLING VOOR TECHNOLOGISCH ONDERZOEK NV), Mol (BE)

(72) Inventors: Wouter Van Hecke, Mol (BE); Helene De Wever, Mol (BE); Lambertus Bouwman, Mol (BE)

(73) Assignee: VITO NV (VLAAMSE INSTELLING VOOR TECHNOLOGISCH ONDERZOEK NV), Mol (BE)

( * ) Notice: Subject to any disclaimer, the term of this patent is extended or adjusted under 35 U.S.C. 154(b) by 155 days.

(21) Appl. No.: 16/318,332

(22) PCT Filed: Jul. 19, 2017

(86) PCT No.: PCT/EP2017/068184
§ 371 (c)(1),
(2) Date: Jan. 16, 2019

(87) PCT Pub. No.: WO2018/015415
PCT Pub. Date: Jan. 25, 2018

(65) Prior Publication Data
US 2019/0249131 A1 Aug. 15, 2019

(30) Foreign Application Priority Data

Jul. 22, 2016 (EP) .................................... 16180832

(51) Int. Cl.
| C12P 7/06 | (2006.01) |
| C12P 7/16 | (2006.01) |
| C12P 7/28 | (2006.01) |
| B01D 61/36 | (2006.01) |
| B01D 5/00 | (2006.01) |
| C12N 1/20 | (2006.01) |
| C12M 1/00 | (2006.01) |
| C12M 1/34 | (2006.01) |
| C10L 1/02 | (2006.01) |

(52) U.S. Cl.
CPC ........... *C12M 43/02* (2013.01); *B01D 61/362* (2013.01); *C12M 21/12* (2013.01); *C12M 41/12* (2013.01); *C12M 41/40* (2013.01); *C12M 47/10* (2013.01); *C12P 7/06* (2013.01); *C12P 7/16* (2013.01); *C12P 7/28* (2013.01); *B01D 5/006* (2013.01); *B01D 2311/04* (2013.01); *B01D 2311/06* (2013.01); *B01D 2311/2646* (2013.01); *B01D 2311/2669* (2013.01); *B01D 2311/2688* (2013.01); *C10L 1/02* (2013.01); *C10L 2200/0469* (2013.01); *C10L 2200/0476* (2013.01); *C10L 2290/544* (2013.01); *C12N 1/20* (2013.01); *Y02E 50/10* (2013.01); *Y02P 20/10* (2015.11)

(58) Field of Classification Search
CPC ...... C12M 43/02; C12M 21/12; C12M 41/12; C12M 41/40; B01D 61/362; B01D 5/006; B01D 2311/2646; B01D 2311/2669; B01D 2311/2688; B01D 2311/04; B01D 2311/06; C12P 7/06; C12P 7/16; C12P 7/28; C12N 1/20
See application file for complete search history.

(56) References Cited

U.S. PATENT DOCUMENTS

| 1,315,585 | A | 9/1919 | Weizmann | |
| 2,386,374 | A | 10/1945 | Weizmann | |
| 5,755,967 | A | 5/1998 | Meagher et al. | |
| 2004/0000521 | A1* | 1/2004 | Vane | C07C 49/08 210/640 |
| 2006/0054485 | A1* | 3/2006 | McGonigle | C02F 1/14 202/155 |

FOREIGN PATENT DOCUMENTS

| EP | 2283141 B1 | 4/2014 |
| WO | 2011/160030 A2 | 12/2011 |
| WO | 2013/086458 A1 | 6/2013 |
| WO | 2015/002913 A1 | 1/2015 |

OTHER PUBLICATIONS

Vane et al., J. Chem. Technol. Biotechnology, 2005, vol. 80, p. 603-629.*
International Search Report and Written Opinion from International Application No. PCT/EP2017/068184, dated Sep. 29, 2017.
W. Van Hecke et al: "Integrated bioprocess for long-term continuous cultivation of Clostridium acetobutylicum coupled to pervaporation with PDMS composite membranes", Bioresource Technology, vol. 111, Feb. 8, 2012 (Feb. 8, 2012), pp. 368-377.
W. Van Hecke et al: "Pervaporative recovery of ABE during continuous cultivation: Enhancement of performance", Bioresource Technology, vol. 129, Nov. 29, 2012 (Nov. 29, 2012), pp. 421-429.
W. Van Hecke et al: "Biobutanol production from C5/C6 carbohydrates integrated with pervaporation: experimental results and conceptual plant design", Journal of Industrial Microbiology and Biotechnology, vol. 43, No. 1, Dec. 14, 2015 (Dec. 14, 2015), pp. 25-36.
M. Marin et al: "Separation of volatile organic compounds from aqueous mixtures by pervaporation with multi-stage condensation", Journal of Food Engineering, vol. 28, No. 3-4, May 1996 (May 1996), pp. 225-238.
J. Liu et al.: "Simulation of the Process for Producing Butanol from Corn Fermentation", Ind. Eng. Chem. Res, 48 (11), 2009, pp. 5551-5557.
W. Van Hecke et al: "Advances in in-situ product recovery (ISPR) in whole cell biotechnology during the last decade", Biotechnology Advances, 32, 2014, pp. 1245-1255.

* cited by examiner

Primary Examiner — Kade Ariani
(74) Attorney, Agent, or Firm — Merchant & Gould P.C.

(57) ABSTRACT

A method for producing products, advantageously solvents, is by fermentation, advantageously multi-stage fermentation. The fermentation is complemented with pervaporation as in situ product recovery technology, combined with a multistage condensation of the permeate. The condensates are separately introduced in the downstream processing to recover the produced products, advantageously solvents. The method for producing products, advantageously solvents, by fermentation is simplified and has an overall improved energy efficiency. A related system uses method for producing products, advantageously solvents, is by fermentation.

18 Claims, 5 Drawing Sheets

METHOD AND SYSTEM FOR PRODUCING PRODUCTS BY FERMENTATION

Figure 1:
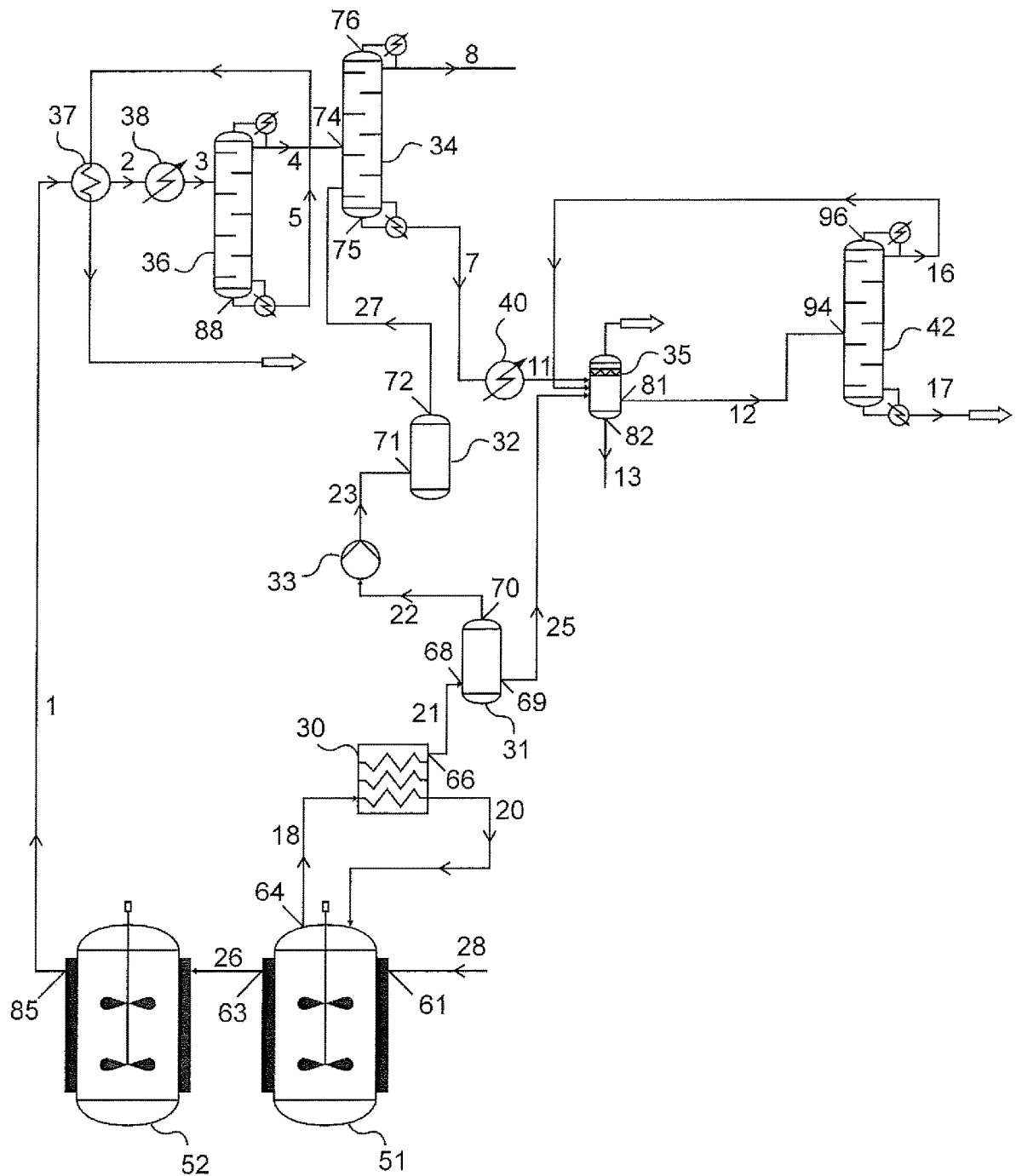

This application is a National Stage Application of International Application No. PCT/EP2017/068184, filed 19 Jul. 2017, which claims benefit of application Ser. No. 16/180,832.4, filed 22 Jul. 2016 in Europe and which applications are incorporated herein by reference. To the extent appropriate, a claim of priority is made to each of the above disclosed applications.

The present invention is related to a method for producing products by fermentation in the presence of microorganisms, a related system and the use thereof. More particularly, the present invention is related to a method for producing solvents by fermentation in the presence of microorganisms, a related system and the use thereof.

Early in the 20th century, the microorganism *Clostridium acetobutylicum* was found to convert carbohydrate containing feedstocks into acetone, ethanol and n-butanol, as described in U.S. Pat. Nos. 1,315,585, and 2,386,374. The method has been referred to since as the acetone n-butanol ethanol (ABE) fermentation process.

As generally known, and for example described in WO2013/086458 and WO2015/002913, n-butanol is an important industrial chemical, useful for example as a solvent, as a feedstock chemical in the plastics industry, as a fuel additive, as an ingredient in formulated products such as cosmetics, and as a food grade extractant in the food and flavor industry. Moreover, as a fuel, n-butanol has several advantages over ethanol. For instance, while n-butanol can be made from the same feedstocks as ethanol, it is, unlike ethanol, compatible with gasoline and diesel at higher ratios. Furthermore, n-butanol can also be used alone as a pure fuel in existing cars without modifications, it has been proposed as a building block to make jet fuel, etc.

A major drawback of n-butanol, however, is its toxicity to the producing culture in the ABE fermentation process, leading to cell inhibition. This is for example discussed in WO2013/086458 and EP 2 283 141. Because of such end product toxicity, solvent productivity is limited and the final concentration of product on a volume basis is low as well. Consequently, energy-intensive distillation operations are used, negatively affecting the economics of recovery of the different products. The high purification cost was one of the major reasons why the ABE fermentation was to a large extent abandoned during the 1950s and 1960s and replaced by petroleum based chemical plants for production of n-butanol and acetone. As such, each year 10 to 12 billion pounds of n-butanol are produced by petrochemical means. However, the depletion of today's fossil fuel stocks, the fluctuations in fossil fuel price and security of energy sources are the driving forces behind the current revival in n-biobutanol production. Accordingly, there is a high demand for efficient and sustainable methods for the production of n-butanol.

As nowadays there is an interest in development of technologies that use renewable resources for fuel production, the ABE fermentation is attracting renewed interest. However, solutions have to be found to avoid or reduce the n-butanol toxicity leading to cell inhibition and the associated low productivities and high purification costs.

In the art, it has already been proposed to alleviate the product inhibition by complementing the fermentation process with in situ product recovery (ISPR) technologies, such as adsorption, pervaporation, gas stripping, or liquid/liquid extraction. In this way, n-butanol is removed from the fermentor as it is produced, thereby allowing the microorganism to produce n-butanol at higher productivity.

WO2011/160030 for example utilizes liquid-liquid extraction as ISPR in a method and system for efficiently producing a fermentative product alcohol such as n-butanol.

Van Hecke, W. et. al., in J. Ind. Microbiol. Biotechnol. 43 (2016) 25-36, integrate organophilic pervaporation as ISPR with n-butanol production from fermentation of C5/C6 carbohydrates, demonstrating a reduction in process flows and providing less energy-intensive downstream processing for recovery of the products.

However, it is observed that by complementing the ABE fermentation process with ISPR as described in the art up to now, the energy consumption and processing cost still remain relatively high (Van Hecke, W. et. al. Biotechnol. Adv. 32 (7) (2014) 1245-1255).

Marin, M. et. al., in J. Food. Eng. 28 (1996) 225-238, describes the separation of volatile organic compounds from aqueous mixtures by pervaporation. The performance of the pervaporation itself is improved by incorporating the pervaporation module with a two-stage condensation. The temperature of the first condenser is thereby described as being always higher than the temperature of the second condenser. The temperature of the first condenser ranges from 0° C. to −20° C.; the temperature of the second condenser ranges from −20° C. to −80° C. A vacuum pump is arranged after the second condenser.

An objective of aspects of the present invention is to provide an improved method for producing products (or product mixtures), more particularly solvents, by fermentation. An objective of further aspects of the present invention is to provide a system for efficiently producing products (or product mixtures), more particularly solvents, by fermentation. It is an object to provide such methods and systems which provide improved energy efficiency. It is also an object to provide such methods and systems which are more cost effective.

According to aspects of the invention, there is therefore provided a method for producing products (or product mixtures) by fermentation.

According to other aspects of the invention, there is provided a system for producing products (or product mixtures) by fermentation.

According to further aspects of the invention, there is provided a solvent (or solvent mixture) obtained by the method of the invention.

According to yet other aspects of the invention, there is provided the use of the system of the invention.

Advantageous aspects of the present invention are set out herein.

Figure 2:
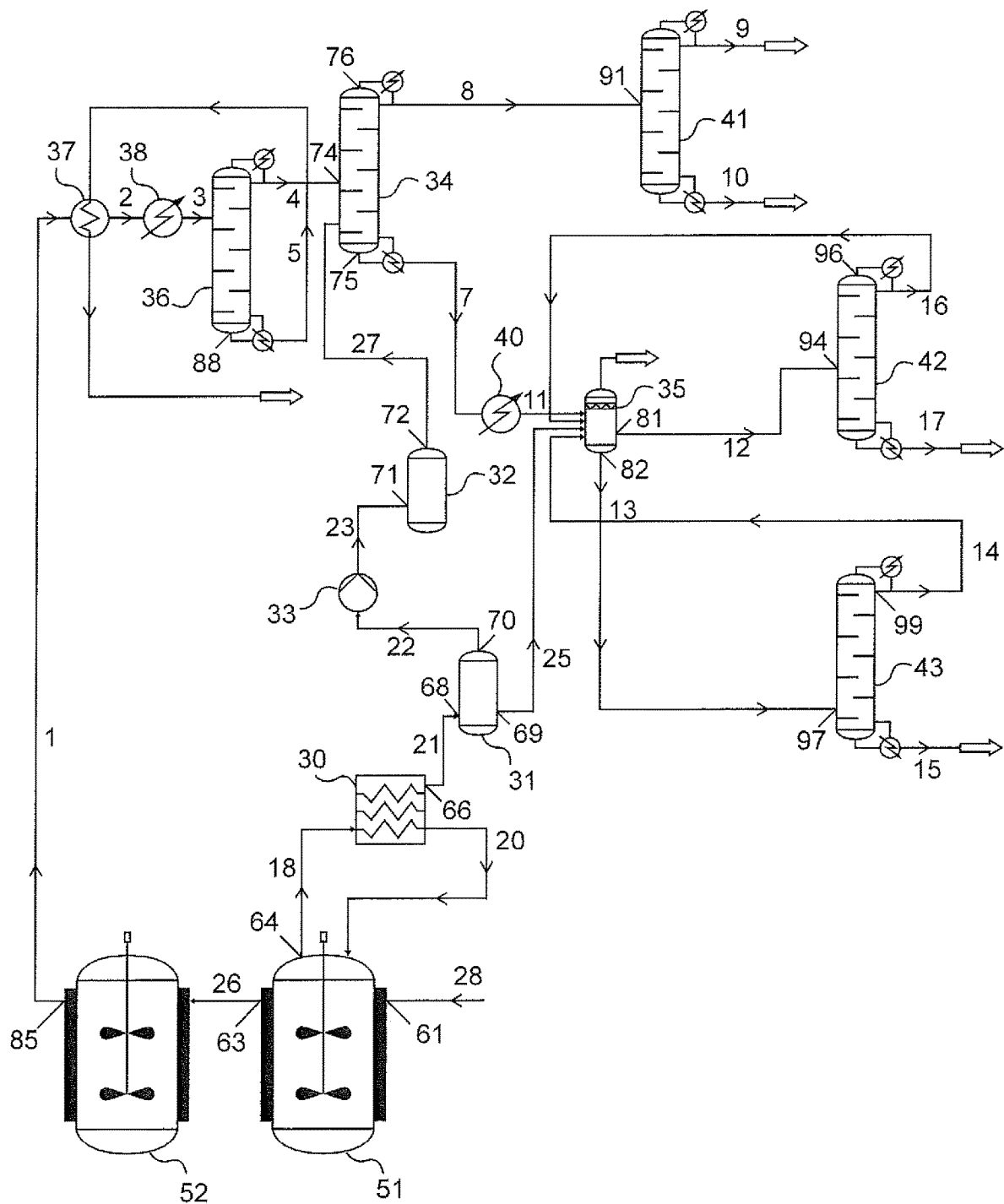
Figure 3:
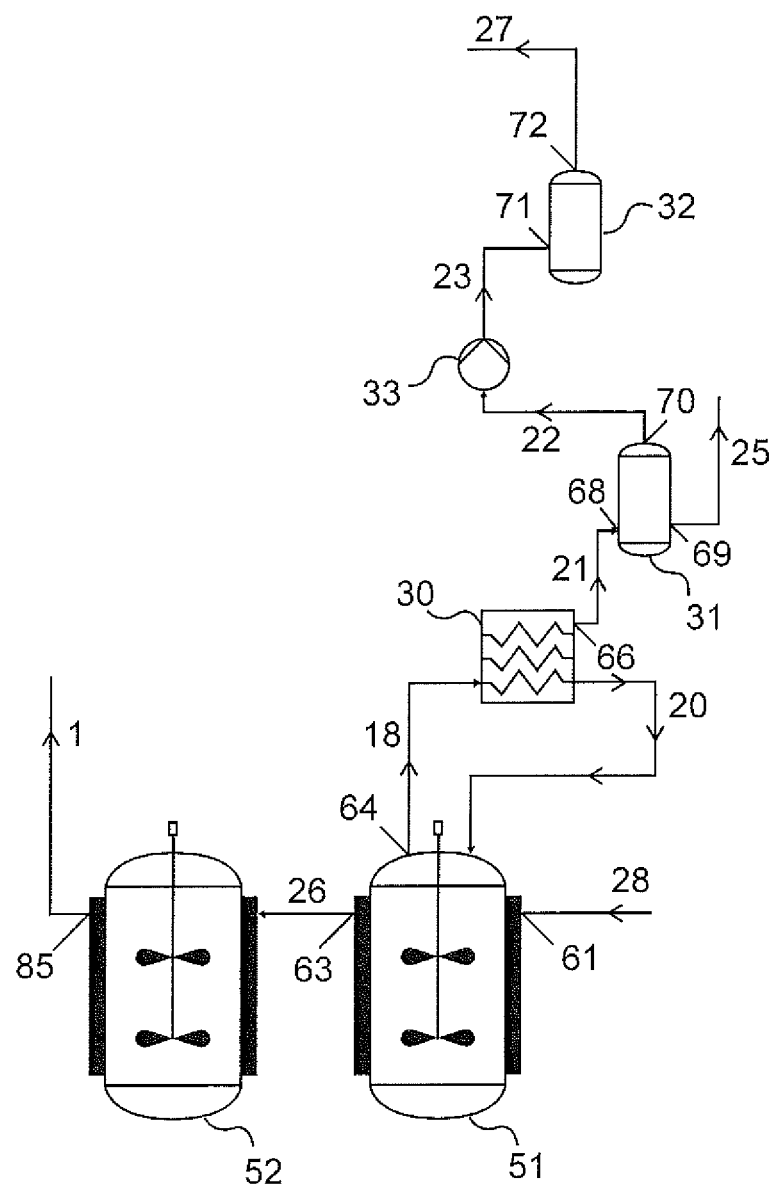
Figure 4:
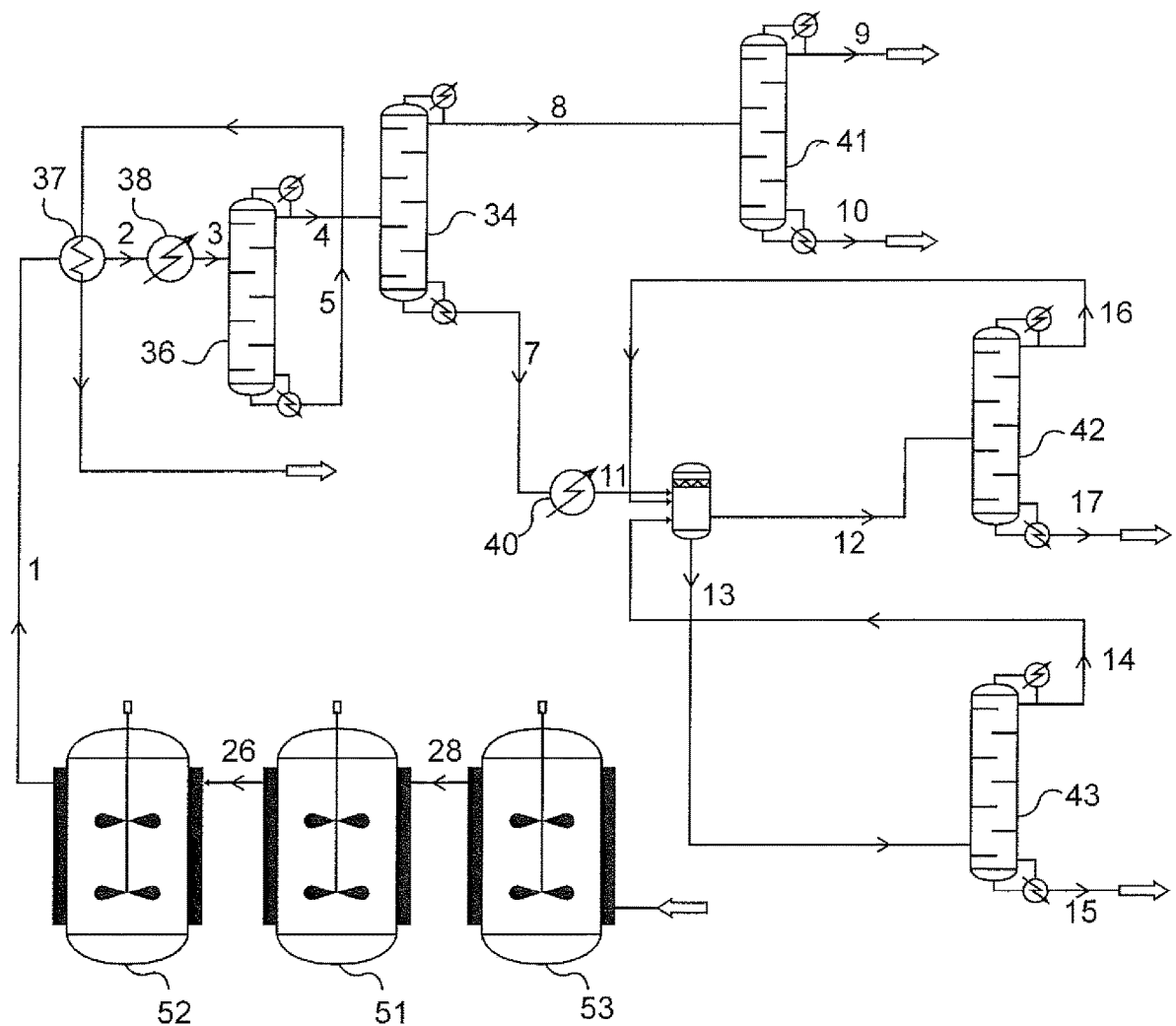
Figure 5:
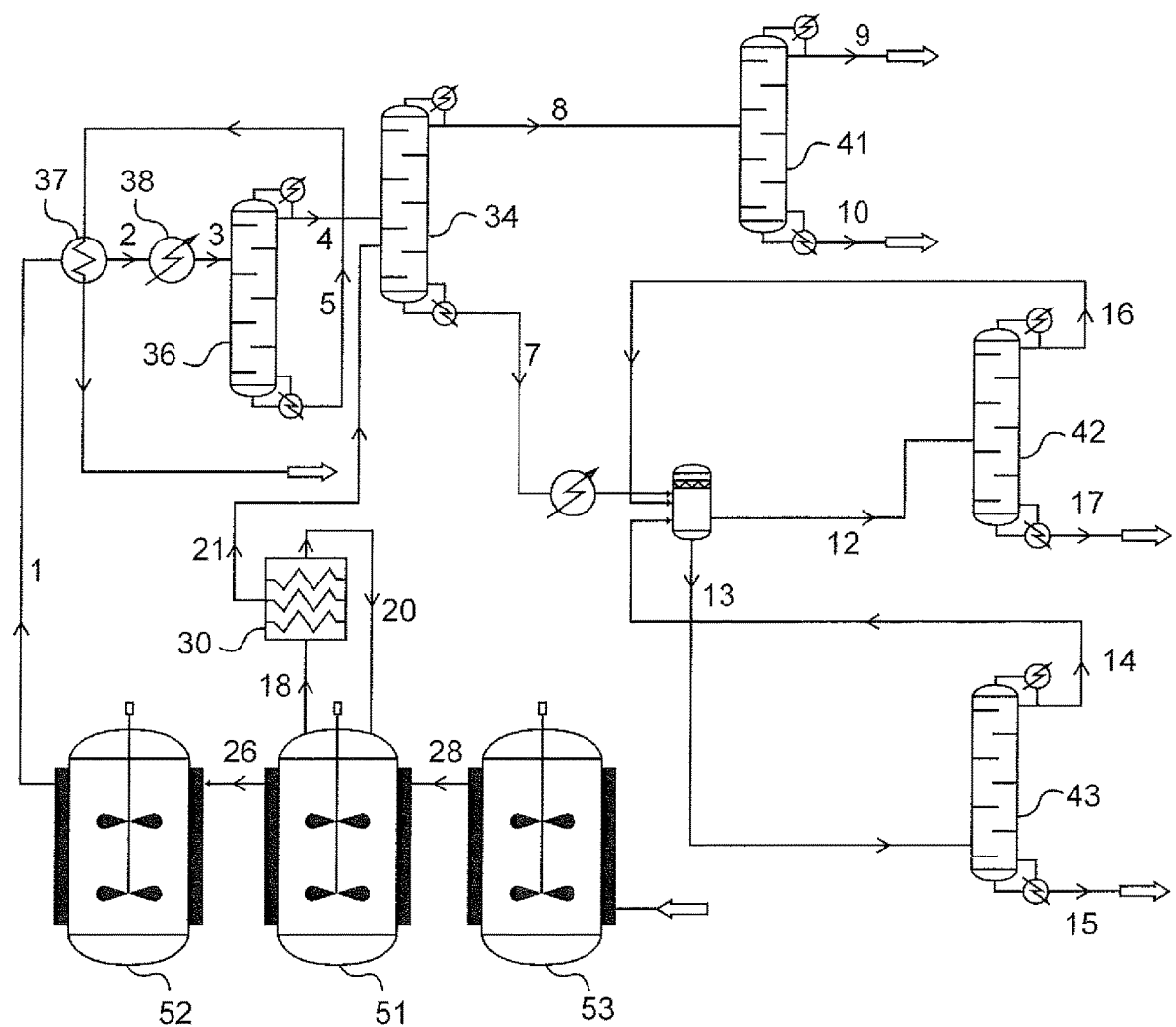

Aspects of the invention will now be described in more detail with reference to the appended drawings, wherein same reference numerals illustrate same features and wherein:

FIG. 1 schematically represents a system as can be used in an embodiment of methods of the present invention;

FIG. 2 schematically represents a system as can be used in another embodiment of methods of the present invention;

FIG. 3 schematically represents an experimental set-up of a multi-stage fermentation with organophilic pervaporation combined with a two-stage condensation of the permeate;

FIG. 4 schematically represents a prior art system used for producing acetone, n-butanol, and ethanol by fermentation;

FIG. 5 schematically represents another prior art system used for producing acetone, n-butanol, and ethanol by fermentation.

Methods for producing products by fermentation according to aspects of the present invention include a pervaporation step in conjunction with a multistage condensation, to further treat the permeate vapour from the pervaporation step, after which the products, advantageously solvents, produced by fermentation are recovered (separated, purified) by further downstream processing. In aspects of the invention, the energy consumption in the whole downstream processing after performing the pervaporation step can be decreased, compared to methods already described in the art. Methods in the art, to the contrary, only describe an improvement of the performance of the pervaporation step itself. Methods and systems of aspects of the invention hence provide an improved energy efficiency and are thus more cost effective.

In the context of the present description, products refer to products or a mixture of products (or product mixture).

In the context of the present description, a solvent refers to an organic solvent or a mixture of organic solvents.

According to an embodiment of aspects of the invention and referring to FIG. 1, a first fermentation step is performed by fermenting a feedstock in a first fermentor (51) in the presence of microorganisms forming a first product stream (18). Advantageously, the first fermentation step is an anaerobic fermentation.

In the context of the present description, a fermentor refers to a fermentation reactor. It can also be referred to as a reaction vessel or a culture vessel.

In the context of the present description, the first product stream (18) refers to the products, advantageously solvents, advantageously organic solvents, formed by the fermentation reaction in the fermentor.

Product stream (18) formed by fermentation is subjected to a pervaporation step, thereby enriching the solvents present in product stream (18) and forming a permeate (or permeate vapour) (21). The pervaporation step is conducted in a pervaporation unit (30) communicating with a first outlet (64) of the first fermentor (51).

Advantageously, an organophilic pervaporation step is performed. The product stream (18) from the first fermentation step is contacted with and selectively vaporized through an organophilic pervaporation membrane, forming a permeate (or permeate vapour) (21).

Advantageously, in aspects of the invention, the pervaporation unit (30) comprises one or more membranes, or one or more membranes modules. Advantageously, the one or more membranes, or the one or more membrane modules, may be of similar or dissimilar type, and may be arranged in any desired configuration, such as one-stage, multistep or multistage, all of which are known for those skilled in the art.

Advantageously, the pervaporation unit (30) comprises a stack of flat sheet membranes, a spiral-wound membrane module, a plate-and-frame module, or a hollow fiber membrane module.

Advantageously, the membranes in the pervaporation unit (30) are organophilic membranes. Suitable organophilic membranes in the pervaporation unit (30) will be apparent for those skilled in the art. For example, the material of the (organophilic) membranes in the pervaporation unit (30) can be polydimethylsiloxane (PDMS), poly(ether-block-amide) (PEBA), or poly[1-(trimethylsilyl)-1-propyne] (PTMSP).

Transport through the pervaporation membrane is induced by maintaining the vapor pressure on the permeate side of the membrane lower than the vapor pressure of the first product stream (18) (or feed liquid). This can be achieved by operating at below atmospheric pressure on the permeate side. A partial vacuum on the permeate side of the membrane can be obtained by relying on the pressure drop that occurs as a result of the cooling and condensation that takes place in a first condenser (31) communicating with a permeate outlet (66) of the pervaporation unit (30), the first condenser (31) having a condensate outlet (69) and a residue outlet (70). Alternatively and preferred, a partial vacuum on the permeate side of the membrane can be obtained by use of a (or of at least one) pump (33) communicating with the residue outlet (70) of the first condenser (31). Advantageously a vacuum pump is used, advantageously a membrane vacuum pump is used.

In aspects of the invention, a pervaporation step is combined with a multistage condensation, advantageously by performing two consecutive condensation steps, to further treat and purify the permeate vapour from the pervaporation step and to recover the produced products, advantageously solvents.

The permeate (21) is sent to the first condenser (31) for partially condensing the permeate. More particularly, a first condensation step is performed, partially condensing the permeate (21), thereby forming a first condensate (25) and a residue stream (22,23). Referring to FIG. 1, the first condensate (25) (in its entirety) exits the first condenser (31) as a bottoms stream (via condensate outlet (69)). The remaining (mainly non-condensed) portion of permeate (21), residue stream (22), exits as the overhead stream from the first condenser (31) (via residue outlet (70)).

Advantageously, in aspects of the invention, the first condenser (31) has one permeate inlet (68) and only two outlets, i.e. one condensate outlet (69) and one residue outlet (70), such that the first condensate (25) exits the first condenser (31) (in its entirety) as a bottoms stream via the one condensate outlet (69), and residue stream (22), i.e. the remaining (mainly non-condensed) portion of permeate (21), exits the first condenser (31) (in its entirety) as the overhead stream via the one residue outlet (70).

Advantageously, the first condensate (25) comprises two (liquid) phases, a solvent rich (top) phase and an aqueous (bottom) phase.

The first condensation step is performed at a first pressure being below atmospheric pressure. Advantageously, the first condensation step is performed at a first pressure being comprised between 5 mbar and 200 mbar, advantageously between 10 mbar and 200 mbar, advantageously between 10 mbar and 150 mbar, advantageously between 10 mbar and 100 mbar. More advantageously, the first condensation step is performed at a first pressure being comprised between 5 mbar and 150 mbar, advantageously between 10 mbar and 100 mbar, advantageously between 10 mbar and 50 mbar, advantageously between 15 mbar and 25 mbar, advantageously between 20 mbar and 25 mbar, advantageously at 20 mbar.

Advantageously, the pervaporation step on the first product stream (18) and the first condensation step partially condensing the permeate (21) are performed at the same first pressure.

Due to the first pressure, advantageously the first pressure and the temperature, at which the first condensation step is performed in a method of aspects of the invention, the permeate (21) is partially condensed, forming the first condensate (25) and residue stream (22). This results in the first condensate (25) being enriched in the less volatile components originating from the first product stream (18) and the residue stream (22) being enriched in the more volatile components originating from the first product stream (18).

After exiting the first condenser (31), the pressure of residue stream (22) is increased to a second pressure higher than the first pressure. The pressure of residue stream (22) is increased by use of a (or of at least one) pump (33)

communicating with the residue outlet (70) of the first condenser (31). Advantageously, a vacuum pump is used, advantageously a membrane vacuum pump is used. Advantageously, the pressure of residue stream (22) is raised to about atmospheric pressure. Alternatively and preferred, the pressure of residue stream (22) is increased by use of at least two pumps (i.e. two, three, or more pumps) connected (arranged) in series between first and second condenser (31,32). Each of the at least two pumps is in communication with a following pump, if any, such that the effluent from the previous pump can be introduced as a feed in the following pump. The inlet of the first pump is communicating with the residue outlet (70) of the first condenser (31) and the outlet of the last (or final) pump in the series of connected pumps is communicating with the residue inlet (71) of the second condenser (32). Each of the at least two pumps is a vacuum pump, advantageously a membrane vacuum pump. For example, three pumps can be arranged in series between first and second condenser (31,32). Using at least two pumps connected in series between first and second condenser (31,32) is minimizing the total pump energy compared to the energy needed when using only one pump (33).

In the context of the present description, the values of the first pressure and second pressure given are absolute pressure values.

The exhaust from the (at least one) pump (33), residue stream (23) being at a second pressure higher than the first pressure, is sent to a second condenser (32).

Alternatively and preferred, the exhaust from the at least two pumps connected in series between first and second condenser (31,32), residue stream (23) being at a second pressure higher than the first pressure, is sent to a second condenser (32).

The residue stream (23) being at a second pressure higher than the first pressure is sent to (residue inlet (71) of) a second condenser (32) for condensing. More particularly, a second condensation step is performed by condensing the residue stream (23) at a second pressure higher than the first pressure forming a second condensate (27) (liquid phase, enriched in the more volatile components originating from the first product stream (18)).

Advantageously, the second condenser (32) is operating at about atmospheric pressure.

By performing the first condensation step, a portion of permeate (21), i.e. residue stream (22), is not completely condensed and exits as the overhead stream from the first condenser (31) (via residue outlet (70)). However, in aspects of the invention, the pressure of residue stream (22) is increased to a second pressure higher than the first pressure. Thereto, a (or at least one) pump (33) is arranged between the first condenser (31) and the second condenser (32), the (at least one) pump (33) being configured to maintain the first condenser (31) at a lower pressure than the second condenser (32). By subsequently subjecting residue stream (23) being at a second pressure higher than the first pressure, to a second condensation step (in a second condenser (32)), the residue stream (23) is almost completely or even fully condensed and exiting (in its entirety) the second condenser (32) as a second condensate (27).

More particularly, due to the second pressure, advantageously the second pressure and the temperature, at which the second condensation step is performed in a method of aspects of the invention, the residue stream (23) is almost completely or even fully condensed and forming the second condensate (27).

As such, by increasing the pressure of the residue stream using a (or at least one) pump (33) arranged between first and second condenser (31,32), advantageously by also performing the first and second condensation step at a same temperature (the temperature being at least 0° C.), the amount of non-condensed permeate, if any at all, is smaller compared to the amount of remaining, non-condensed permeate using methods (or systems) described in the art operating at similar temperatures as used in the two-stage condensation set-up according to aspects of the present invention. The present invention hence also provides a more efficient condensation performed in the downstream processing, i.e. being more efficient in terms of yield of condensate, compared to methods (or systems) (operating at similar temperatures) described in the art.

Advantageously, in aspects of the invention, the second condenser (32) has one residue inlet (71) and only one condensate outlet (72), such that the second condensate (27) exits the second condenser (32) (in its entirety) as the overhead stream via the one condensate outlet (72).

Advantageously, the first condensation step and second condensation step are performed at a same cooling temperature. Advantageously, the first condensation step and second condensation step are performed at a temperature being comprised between 0° C. and 20° C., advantageously between 0° C. and 15° C., advantageously between 0° C. and 10° C., advantageously between 1° C. and 8° C., advantageously between 2° C. and 5° C., advantageously at 2° C.

Advantageously, a coolant is provided in the first and second condenser (31,32) for cooling the condensers. Advantageously, the first and second condenser (31,32) are cooled (with a coolant) to a temperature being comprised between 0° C. and 20° C., advantageously between 0° C. and 15° C., advantageously between 0° C. and 10° C., advantageously between 1° C. and 8° C., advantageously between 2° C. and 5° C., advantageously at 2° C. Advantageously, water is used as the coolant.

Advantageously, the coolant is water, or water comprising ethylene glycol.

The coolant can, for example, be introduced at or near the top of each of the condensers, flowing down and exiting the condenser at the bottom, providing cooling over the length of the condenser. The stream of coolant exiting the first condenser can, for example, be further used to be introduced at or near the top of the second condenser.

The second condensate (27) exiting the second condenser (32) is supplied as feed to a first distillation column (34) communicating with a condensate outlet (72) of the second condenser (32). The second condensate (27) is distilled to produce a stream (8) as the overhead stream, enriched in a first range of solvents, and a liquid stream (7) as a bottoms stream, depleted in the first range of solvents.

Alternatively, the exhaust from (the at least one) pump (33), residue stream (23), can be sent directly to the first distillation column (34) communicating therewith, without being (further) condensed in the second condenser (32).

In the context of the present description, a distillation step is carried out in a distillation column, advantageously a multistage distillation column comprising a number of theoretical stages ranging between 6 and 35.

Subsequently, in aspects of the invention, liquid stream (7) exiting the first distillation column (34) is sent to a decanter (35) communicating with a first outlet (75) of the first distillation column (34). Advantageously, at least one heat exchanger is arranged between a first outlet (75) of the first distillation column (34) and the decanter (35). Advantageously, the liquid stream (7) is passing through a heat exchanger (40) before arriving in the decanter (35), in order to arrange the temperature of the liquid stream (7) to a temperature suitable for decantation. In aspects of the invention, a suitable temperature for decantation depends on the products, advantageously solvents, to separate and will be apparent for those skilled in the art. Advantageously, the exhaust (11) from the heat exchanger (40) has a temperature comprised between 35° C. and 45° C.

In a method of aspects of the invention, the liquid stream (7) is physically brought together (or combined) in the decanter (35) with the first condensate (25) (enriched in the less volatile components) exiting the first condenser (31). More particularly, the first condensate (25) exiting the first condenser (31) (in its entirety) is completely sent to the decanter (35) as well, the decanter (35) communicating with the condensate outlet (69) of the first condenser (31). The first condensate (25) is then decanted together with the liquid stream (7) from the first distillation column (34) forming (or being separated in) a solvent rich phase (12) enriched in a second range of solvents, and an aqueous phase (13).

In aspects of the invention, the first and second condensates (25,27), obtained by the multistage condensation, are separately introduced and purified in the downstream processing to recover the produced products, advantageously solvents. Due to the fact that the first condensate (25), exiting (in its entirety) the first condenser (31), is completely sent to a decanter (35), and the second condensate (27), exiting the second condenser (32), is further supplied as feed to a first distillation column (34) for further purification, the energy consumption in said first distillation column (34) can be decreased, compared to methods described in the art. As such, the overall energy consumption in the downstream processing after performing the pervaporation step is decreased, compared to methods (and systems) described in the art (in fact, the methods and systems in the art are only describing an improvement of the performance of the pervaporation step itself). A method and system in aspects of the invention hence provide an improved energy efficiency and are thus more cost effective.

The fermentation in aspects of the present invention is a one-stage fermentation. Advantageously (or optionally), the fermentation is a multi-stage fermentation. Advantageously, the multi-stage fermentation is at least a two-stage fermentation (i.e. the multi-stage fermentation is a two-, three-, or four-stage fermentation, or the multi-stage fermentation comprises even more than four stages or fermentation steps).

The fermentation step(s) in a method of aspects of the present invention is (are) performed by fermenting a feedstock in the presence of microorganisms, advantageously by fermentation in the presence of microorganisms of the *Clostridium* genus (commonly referred to as *Clostridia* spp.), or in the presence of genetically modified organisms derived thereof. Advantageously a feedstock is fermented in the presence of microorganisms of *Clostridium acetobutylicum*, *Clostridium beijerinckii*, *Clostridium saccharobutylicum*, *Clostridium saccharoperbutylacetonicum*, *Clostridium pasteurianum*, or the like, advantageously in the presence of microorganisms of *Clostridium acetobutylicum*.

Advantageously, the fermentation step(s) in aspects of the present invention is (are) carried out at a temperature comprised between 30° C. and 45° C., advantageously between 30° C. and 40° C., advantageously between 32° C. and 38° C., advantageously between 35° C. and 37° C. In other words, the fermentor(s) is (are) run at a temperature comprised between 30° C. and 45° C., advantageously between 30° C. and 40° C., advantageously between 32° C. and 38° C., advantageously between 35° C. and 37° C.

Advantageously, the feedstock used in the fermentation step(s) in aspects of the invention originates from sugar cane, corn mash, wheat, or other carbohydrate containing feedstocks (such as hydrolysates containing C5/C6 carbohydrates (such as starch, glucose, xylose), lignocellulosic hydrolysates, or hydrolysates from pulp and paper industry). In addition, or alternatively, the feedstock can originate from glycerol e.g. derived as a byproduct from biodiesel production (biodiesel-derived glycerol); or from gaseous substrates such as $CO_2$ or Syngas.

Advantageously, the feedstock in the fermentation step(s) in aspects of the invention is subjected to an anaerobic fermentation.

Advantageously, the pH in the fermentor(s) during the fermentation step(s) in aspects of the invention is comprised between 4.0 and 6.0, advantageously between 4.0 and 5.5, advantageously between 4.5 and 5.5, advantageously between 4.5 and 5.0.

A method in aspects of the invention can be performed in a batch, fed-batch, or continuous manner, i.e. the feedstock is provided (or introduced) in the fermentor(s) on a batch, fed-batch, or continuous basis.

Advantageously (or optionally), as for example shown in FIG. 1, the effluent (26) from the first fermentation step is introduced into a second fermentor (52). The second fermentor (52) is communicating with a second outlet (63) of the first fermentor (51).

The effluent (26) is subjected to a second fermentation step, further converting residual feedstock from the first fermentation to products, advantageously solvents, forming a second product stream (1).

More advantageously, a second fermentor (52) is (optionally) used to allow a conversion of the residual carbohydrate in stream (26), and to allow maximum solvent titers, higher than can be obtained in a one-stage fermentation process. The improved carbohydrate conversion will lower the substrate costs and the higher solvent titers will decrease the cost for further recovery of residual solvents.

Advantageously, in a method of aspects of the invention, the second product stream (1) is passed as a feed to a steam stripper (36) communicating with an outlet (85) of the second fermentor (52).

In aspects of the invention, fermentor effluent can be sent to a centrifuge for cell/particle removal prior to sending the (cell/particle-free) effluents to a steam stripper or alternative end-of-pipe processes. Suitable forms of alternative (more energy efficient) end-of-pipe processes will be apparent for those skilled in the art. Recovery of residual solvents can for example be performed by absorption, adsorption, extraction (instead of by steam stripping).

Advantageously, in a method of aspects of the invention, the top stream (4) exiting the steam stripper (36) is then sent to and distilled (or purified) in first distillation column (34) (the steam stripper (36) communicating with an inlet (74) of the first distillation column (34)), together with the second condensate (27) coming from the second condenser (32) (the decanter (35) communicating with the condensate outlet (69) of the first condenser (31)), to produce stream (8) and liquid stream (7).

Advantageously, in a method of aspects of the invention, at least one heat exchanger is arranged between the outlet (85) of the second fermentor (52) and the steam stripper (36). More advantageously, a first and second heat exchanger (37,38), are arranged between the outlet (85) of the second fermentor (52) and the steam stripper (36).

In the context of the present description, a steam stripper refers to a beer stripper or steam distillation apparatus, known by those skilled in the art.

In an alternative embodiment of aspects of the invention (not shown), the steam stripper (36) is communicating with a second outlet (63) of the first fermentor (51). The effluent (26) from the first fermentation step is introduced as a feed into the steam stripper (36) without being subjected to a second fermentation. Advantageously, at least one heat exchanger is arranged between a second outlet (63) of the first fermentor (51) and the steam stripper (36). More advantageously, a first and second heat exchanger (37,38), are arranged between a second outlet (63) of the first fermentor (51) and the steam stripper (36). Advantageously, the top stream (4) exiting the steam stripper (36) is sent to and distilled in first distillation column (34) (the steam stripper (36) communicating with an inlet (74) of the first distillation column (34)), together with the second condensate (27) coming from the second condenser (32) (the decanter (35) communicating with the condensate outlet (69) of the first condenser (31)), to produce stream (8) and liquid stream (7).

Advantageously, in a method of aspects of the invention, before arriving into the steam stripper (36), the feed (1, or alternatively 26) is heated to a temperature suitable for steam stripping.

In aspects of the invention, a suitable temperature for steam stripping depends on the products, advantageously solvents, to separate and will be apparent for those skilled in the art.

Advantageously, the feed (1, or alternatively 26) sent to the steam stripper (36) is heated before arriving to the steam stripper (36). The feed (1, or alternatively 26) is first heated by (counter current) heat exchanger (37), to a temperature comprised between 75° C. to 85° C., after which the heated feed (2) is further heated, by heat exchanger (38), to a temperature comprised between 90° C. to 95° C., after which the heated feed (3) is sent to the steam stripper (36).

Performing the first fermentation step a first product stream (18) is formed, advantageously solvents are formed.

Advantageously, performing the (anaerobic) second fermentation step further converts residual feedstock from the first fermentation to products, advantageously solvents.

Advantageously, in a method of aspects of the invention, the first condensate (25) obtained after partially condensing the permeate (21), exiting the first condenser (31) as a bottoms stream, comprises two phases, a solvent rich (top) phase and an aqueous (bottom) phase, advantageously the solvent rich phase comprises n-butanol and the aqueous phase comprises water. The residue stream (22) (remaining portion of permeate) obtained after partially condensing the permeate (21), exiting the first condenser (31) as an overhead stream, comprises acetone, n-butanol, ethanol, and water. Stream (8) obtained after distilling the second condensate (27), exiting the first distillation column (34) as an overhead stream, comprises acetone and ethanol. The liquid stream (7) obtained after distilling the second condensate (27), exiting the first distillation column (34) as a bottoms stream comprises two phases, a solvent rich phase and an aqueous phase, advantageously the solvent rich (top) phase comprises n-butanol and the aqueous (bottom) phase comprises water. The phase (12) obtained after decanting the first condensate (25) together with the liquid stream (7) comprises n-butanol. The phase (13) obtained after decanting the first condensate (25) together with the liquid stream (7), exiting the decanter (35) as a bottoms stream, is an aqueous phase. Advantageously, the aqueous phase comprises between 3% to 15% by volume n-butanol, advantageously between 5% to 10% by volume n-butanol, advantageously 7% by volume n-butanol.

In a method of aspects of the invention, the first condensate (25) (obtained after partially condensing the permeate (21), exiting the first condenser (31) as a bottoms stream) and the liquid stream (7) (obtained after distilling the second condensate (27), exiting the first distillation column (34) as a bottoms stream) both comprise the same components. More particularly, the first condensate (25) and the liquid stream (7) both comprise two phases, a solvent rich phase and an aqueous phase, advantageously the solvent rich (top) phase comprises mainly n-butanol and the aqueous (bottom) phase comprises mainly water. As such, the first condensate (25) and the liquid stream (7) can be treated together and are sent to the same decanter (35) in which the first condensate (25) is decanted together with the liquid stream (7). As such, the downstream processing after performing the pervaporation step is simplified, compared to methods described in the art (methods and systems in the art only describing an improvement of the performance of the pervaporation step itself). Moreover, due to this simultaneous treatment (by decantation) of both streams (7,25) together, the energy consumption in aspects of the invention can be further lowered, in addition to the decrease in energy in the first distillation step (in first distillation column (34)) due to the separate treatment of the condensates (25,27), compared to methods described in the art. In case the first condensate (25) is more enriched in n-butanol compared to stream (7), the energy consumption in second and third distillation columns (42,43) can be further decreased.

According to aspects of the invention, a simplified method and system for producing products by fermentation are thus provided having an overall improved energy efficiency and being more cost effective, compared to methods and systems described in the art. The beneficial effects are advantageously obtained by combining fermentation with organophilic pervaporation and a subsequently multistage (advantageously two-stage) condensation.

Advantageously, in a method of aspects of the invention,
the first condensate (25) comprises a solvent rich phase comprising n-butanol and an aqueous phase comprising water;
the residue stream (22) comprises acetone, n-butanol, ethanol, and water;
the first range of solvents in stream (8) comprises acetone and ethanol;
the second range of solvents in the phase (12) formed by decantation comprises n-butanol.

More advantageously,
the first fermentation step is performed by fermenting a feedstock in the presence of microorganisms of *Clostridium acetobutylicum*;
performing the first condensation step forms a first condensate (25) comprising n-butanol and water, and a residue stream (22) comprising acetone, n-butanol, ethanol, and water,
the first condensation step is performed at a first pressure being comprised between 5 mbar and 200 mbar, advantageously between 10 mbar and 100 mbar,
the first and second condensation steps are performed at the same cooling temperature, the temperature being comprised between 0° C. and 20° C., advantageously between 0° C. and 10° C.;
the second condensate (27) is distilled to produce a stream (8) enriched in acetone and ethanol, and a liquid stream (7) depleted in acetone and ethanol;

the first condensate (25) is decanted together with the liquid stream (7) forming a phase (12) enriched in n-butanol and an aqueous phase (13).

More advantageously, the first condensation step is performed at a first pressure being comprised between 10 mbar and 100 mbar, and the first and second condensation steps are performed at the same cooling temperature, the temperature being comprised between 0° C. and 10° C.

Advantageously, in a method of aspects of the invention, the phase (12) obtained after decanting the first condensate (25) together with the liquid stream (7) is sent to a second distillation column (42), communicating with a first outlet (81) of the decanter (35), and is further purified by distillation, forming a first solvent, advantageously a substantially pure first solvent. The first solvent (17) exits the second distillation column (42) as a bottoms stream. Advantageously, (substantially pure) n-butanol is formed. Advantageously, the obtained n-butanol has a purity comprised between 99.0% (w/w) and 99.9% (w/w), advantageously between 99.5% (w/w) and 99.9% (w/w), advantageously between 99.7% (w/w) and 99.9% (w/w), advantageously a purity of 99.8% (w/w).

The produced (substantially pure) n-butanol in aspects of the invention can be used as an intermediate in chemical industry. For example, the produced n-butanol can be used as a solvent, as a feedstock chemical in the plastics industry, as an ingredient in formulated products such as cosmetics, as a food grade extractant in the food and flavor industry, as a fuel, or as a fuel additive.

The top stream (16) exiting second distillation column (42) from the distillation of phase (12) can be recycled back to the decanter (35) for decantation, the second distillation column (42) communicating with an inlet of the decanter (35).

Referring to FIG. 2, in an embodiment of aspects of the invention, the aqueous phase (13) formed by decantation of the first condensate (25) together with the liquid stream (7), exiting the decanter (35) as a bottoms stream, can be sent to a third distillation column (43), communicating with a second outlet (82) of the decanter (35), to be further purified by distillation, forming an aqueous phase (15) depleted from (substantially pure) first solvent. Advantageously, aqueous phase (15) comprises only trace amounts of (organic) solvents, advantageously aqueous phase (15) comprises mainly water depleted from n-butanol. The aqueous phase (15) exits the third distillation column (43) as a bottoms stream. The top stream (14) (or overhead stream) exiting third distillation column (43) from the distillation of the aqueous phase (13) can be recycled back to the decanter (35) for decantation, the third distillation column (43) communicating with an inlet of the decanter (35).

In an alternative embodiment of aspects of the invention (not shown), the aqueous phase (13) formed by decantation of the first condensate (25) together with the liquid stream (7), exiting the decanter (35) as a bottoms stream, can be sent to an extraction unit (not shown). Advantageously, in the extraction unit, n-butanol is extracted out of water using a (bio)diesel or another fuel as extractant. This results in the production of a n-butanol enriched (bio)fuel, which can be further used as such.

Advantageously, in a method of aspects of the invention, stream (8) obtained after distilling the second condensate (27), exiting the first distillation column (34) as an overhead stream, comprises mainly acetone and ethanol. Advantageously, stream (8) comprising acetone and ethanol is not further purified such that the obtained solution comprising acetone and ethanol can directly be used in further chemical reactions. Alternatively, stream (8) comprising acetone and ethanol is further purified in (substantially pure) acetone and an azeotropic mixture of ethanol.

Referring to FIG. 2, in an embodiment of aspects of the invention, stream (8) obtained after distilling the second condensate (27), exiting the first distillation column (34) as an overhead stream, can be sent to fourth distillation column (41), communicating with a second outlet (76) of the first distillation column (34), and can be further purified by distillation, forming a stream (9) enriched in a (substantially pure) second solvent and a stream (10) enriched in a third solvent (and being depleted in the second solvent). Stream (9) exits the fourth distillation column (41) as a top stream, stream (10) exits the distillation column (41) as a bottoms stream. Advantageously, a stream (9) enriched in a second solvent, advantageously acetone, is formed. Advantageously, a stream (9) of substantially pure acetone is formed. Advantageously, the obtained acetone has a purity comprised between 98.0% (w/w) and 99.9% (w/w), advantageously between 98.5% (w/w) and 99.5% (w/w), advantageously between 99.0% (w/w) and 99.5% (w/w). Advantageously, a stream (10) enriched in a third solvent, advantageously ethanol, is formed. Advantageously, a stream (10) of ethanol is formed. Advantageously, stream (10) is an azeotropic mixture (or azeotropic solution) comprising between 85% and 90% by volume ethanol and between 10% and 15% by volume water, advantageously between 86% and 88% by volume ethanol and between 12% and 14% by volume water, advantageously 87% by volume ethanol and 13% by volume water.

Advantageously, in a method of aspects of the invention, a third (or further) (anaerobic) fermentation step is performed before performing the first fermentation step. The third fermentor (not shown in FIGS. 1 to 3) is communicating with a first inlet (61) of the first fermentor (51). The effluent (28) from the third fermentation step is introduced as feed in the first fermentor (51) for further performing a fermentation step, possibly followed by another fermentation step in the subsequent fermentor (52) communicating with a second outlet (63) of the first fermentor (51).

Advantageously, in a method of aspects of the invention, after performing the pervaporation step, a non-permeating portion of first product stream (18) is returned as a liquid residue stream (20) to the first, second, or third (or further) fermentor, advantageously to the first fermentor (51).

Advantageously, in a method of aspects of the invention, the bottoms stream (5) exiting the steam stripper (36) can be sent to a multiple-effect evaporator system (not shown) communicating with an outlet (88) of the steam stripper (36), for further concentrating this stream. Advantageously, the multiple-effect evaporator system is a 5-effect evaporator system. Advantageously, before arriving into the multiple-effect evaporator system, stream (5) is passed through a (countercurrent) heat exchange system (37), where the heat is recovered from this spent and stripped stream (5). The recovered heat can be used to heat the feed (1, or alternatively 26) passing to the steam stripper (36).

In aspects of the invention, a suitable temperature for performing the first to fourth distillation and the steam stripping depends on the products, advantageously solvents, to separate and will be apparent for those skilled in the art.

Advantageously, in a method of aspects of the invention, the first fermentation step is performed by fermenting a feedstock, advantageously glycerol, in the presence of microorganisms of *Clostridium pasteurianum* forming 1,3-propanediol remaining in the fermentation broth and a first product stream (18) comprising n-butanol, ethanol, and water;

performing the first condensation step forms a first condensate (25) comprising n-butanol and water, and a residue stream (22) comprising n-butanol, ethanol, and water, the first condensation step is performed at a first pressure being comprised between 5 mbar and 200 mbar, advantageously between 10 mbar and 100 mbar;

the first and second condensation steps are performed at the same cooling temperature, the temperature being comprised between 0° C. and 20° C., advantageously between 0° C. and 10° C.;

the second condensate (27) is distilled to produce a stream (8) enriched in ethanol, and a liquid stream (7) depleted in ethanol;

the first condensate (25) is decanted together with the liquid stream (7) forming a phase (12) enriched in n-butanol and an aqueous phase (13).

Such fermentation produces 1,3-propanediol, butanol, and ethanol. The fermentation is referred to as PBE fermentation. No acetone is produced in the PBE fermentation. The formed 1,3-propanediol remains in the fermentation broth (1,3-propanediol being much less volatile than butanol).

More advantageously, in the PBE fermentation, the first condensation step is performed at a first pressure being comprised between 10 mbar and 100 mbar, and the first and second condensation steps are performed at the same cooling temperature, the temperature being comprised between 0° C. and 10° C.

More advantageously, biodiesel-derived glycerol (commonly referred to as crude glycerol) is used as feedstock for the PBE fermentation.

Phase (12) enriched in n-butanol formed by decantation can be purified by distillation, forming n-butanol (as first solvent (17)).

Advantageously, in a method of aspects of the invention, the first condensate (25) comprises n-butanol and water;

the residue stream (22) comprises isopropanol, n-butanol, ethanol, and water;

the first range of solvents in stream (8) comprises isopropanol and ethanol;

the second range of solvents in the phase (12) formed by decantation comprises n-butanol.

Such fermentation produces isopropanol, butanol, and ethanol. The fermentation is referred to as IBE fermentation. No acetone is produced in the IBE fermentation.

More advantageously, in such IBE fermentations of aspects of the invention, the first fermentation step is performed by fermenting a feedstock in the presence of microorganisms of *Clostridium acetobutylicum* or *Clostridium beijerinckii*;

performing the first condensation step forms a first condensate (25) comprising n-butanol and water, and a residue stream (22) comprising isopropanol, n-butanol, ethanol, and water, the first condensation step is performed at a first pressure being comprised between 5 mbar and 200 mbar, advantageously between 10 mbar and 100 mbar;

the first and second condensation steps are performed at the same cooling temperature, the temperature being comprised between 0° C. and 20° C., advantageously between 0° C. and 10° C.;

the second condensate (27) is distilled to produce a stream (8) enriched in isopropanol and ethanol, and a liquid stream (7) depleted in isopropanol and ethanol;

the first condensate (25) is decanted together with the liquid stream (7) forming a phase (12) enriched in n-butanol and an aqueous phase (13).

Even more advantageously, in the IBE fermentation, the first condensation step is performed at a first pressure being comprised between 10 mbar and 100 mbar, and the first and second condensation steps are performed at the same cooling temperature, the temperature being comprised between 0° C. and 10° C.

Phase (12) enriched in n-butanol formed by decantation can be purified by distillation, forming n-butanol (as first solvent (17)).

Stream (8) enriched in isopropanol and ethanol can be purified by distillation, forming a stream (9) enriched in ethanol, and a stream (10) enriched in isopropanol.

In further aspects, the present invention is related to a solvent, advantageously n-butanol, acetone, or ethanol, advantageously n-butanol, as obtained, or obtainable, by the above methods of aspects of the invention. 1,3-propanediol, n-butanol, or ethanol; or isopropanol, n-butanol, or ethanol are obtainable by methods of aspects of the invention as well. The obtained solvent, advantageously n-butanol, has a purity comprised between 99.0% (w/w) and 99.9% (w/w), advantageously between 99.5% (w/w) and 99.9% (w/w), advantageously between 99.7% (w/w) and 99.9% (w/w), advantageously a purity of 99.8% (w/w).

Systems for producing products by fermentation according to aspects of the present invention include a pervaporation unit in conjunction with multiple condensers, advantageously two condensers.

As illustrated schematically in FIG. 1, a system according to the present invention comprises:

a first fermentor (51);

a pervaporation unit (30) communicating with a first outlet (64) of the first fermentor (51); characterized in that the system comprises:

a first condenser (31) communicating with a permeate outlet (66) of the pervaporation unit (30), and having a condensate outlet (69) and a residue outlet (70);

a second condenser (32) communicating with the residue outlet (70) of the first condenser (31);

a (or at least one) pump (33) arranged between the first condenser (31) and the second condenser (32), wherein the (at least one) pump (33) is configured to maintain the first condenser (31) at a lower pressure than the second condenser (32);

a first distillation column (34) communicating with a condensate outlet (72) of the second condenser (32);

a decanter (35) communicating with the condensate outlet (69) of the first condenser (31) and with a first outlet (75) of the first distillation column (34).

Advantageously, in aspects of the invention, the pervaporation unit (30) comprises one or more membranes, or one or more membrane modules. Advantageously, the one or more membranes, or the one or more membrane modules, may be of similar or dissimilar type, and may be arranged in any desired configuration, such as one-stage, multistep or multistage, all of which are known for those skilled in the art.

Suitable forms of membranes will be apparent for those skilled in the art.

Advantageously, in aspects of the invention, the membranes in the pervaporation unit (30) are formed as flat sheets, hollow fibers, tubular membranes, or any other convenient form.

Advantageously, in aspects of the invention, the membranes are housed in any appropriate module configuration. Suitable membrane modules, as well as the preparation thereof, will be apparent for those skilled in the art. For example, the membrane module(s) in the pervaporation unit (30) can be a stack of flat sheet membranes, a spiral-wound membrane module, a plate-and-frame module, or a hollow fiber membrane module.

Advantageously, the membranes in the pervaporation unit (30) are organophilic membranes. Suitable organophilic membranes will be apparent for those skilled in the art. For example, the material of the (organophilic) membranes in the pervaporation unit (30) can be polydimethylsiloxane (PDMS), poly(ether-block-amide) (PEBA), or poly[1-(trimethylsilyl)-1-propyne] (PTMSP).

Advantageously, the material of the first condenser (31) and the second condenser (32) is selected from the group consisting of glass, or (stainless) steel.

Advantageously, the (at least one) pump (33) is a vacuum pump, advantageously a membrane vacuum pump. In the alternative embodiment where at least two pumps (i.e. two, three, or more pumps) are connected (arranged) in series between first and second condenser (31,32), each of the at least two pumps is a vacuum pump, advantageously a membrane vacuum pump as well.

Advantageously, the system is configured for controlling the temperature of the first and second condenser (31,32), the temperature being comprised between 0° C. and 20° C., advantageously between 0° C. and 15° C., advantageously between 0° C. and 10° C., advantageously between 1° C. and 8° C., advantageously between 2° C. and 5° C., advantageously being at 2° C. Advantageously, the system is configured for controlling the temperature of the first and second condenser (31,32) to be the same cooling temperature.

A control unit (comprising sensors) can for example be provided in a system of aspects of the invention, controlling (or maintaining) the temperature of the first and second condenser (31,32) (to be at the same cooling temperature), the temperature being comprised between 0° C. and 20° C., advantageously between 0° C. and 15° C., advantageously between 0° C. and 10° C., advantageously between 1° C. and 8° C., advantageously between 2° C. and 5° C., advantageously at 2° C.

Advantageously, at least one heat exchanger (40) is arranged between a first outlet (75) of the first distillation column (34) and the decanter (35). Referring to FIG. 1, heat exchanger (40) is arranged between a first outlet (75) of the first distillation column (34) and the decanter (35).

Advantageously (or optionally), in aspects of the invention, the system comprises multiple fermentors (i.e. more than one fermentor). Advantageously, the system comprises at least two fermentors (i.e. at least first and second fermentor (51,52); or two, three, four, or more fermentors). The two, three, four, or more fermentors can have a same or a different volume. Each of the at least two fermentors can be in communication with a following fermentor, if any, such that the effluent from the previous fermentor can be introduced as a feed in the following fermentor so as to perform a multistage fermentation.

Advantageously, as illustrated schematically in FIG. 1, a system of the invention further comprises:
a second fermentor (52) communicating with a second outlet (63) of the first fermentor (51);
a steam stripper (36) communicating with an outlet (85) of the second fermentor (52) and communicating with an inlet (74) of the first distillation column (34).

In an alternative embodiment, a system of aspects of the invention (not shown) comprises a steam stripper (36) communicating with a second outlet (63) of the first fermentor (51) and communicating with an inlet (74) of the first distillation column (34).

Advantageously, at least one heat exchanger is arranged between the outlet (85) of the second fermentor (52) and the steam stripper (36), alternatively between the second outlet (63) of the first fermentor (51) and the steam stripper (36). More advantageously, a first and second heat exchanger (37,38), are arranged between the outlet (85) of the second fermentor (52) and the steam stripper (36), alternatively between the second outlet (63) of the first fermentor (51) and the steam stripper (36).

Advantageously, a system of aspects of the invention comprises a multiple-effect evaporator system. Advantageously, an outlet (88) of the steam stripper (36) is communicating with a multiple-effect evaporator system (not shown). Advantageously, the multiple-effect evaporator system is a 5-effect evaporator system. Advantageously, at least one heat exchanger (37) is arranged between the outlet (88) of the steam stripper (36) and the multiple-effect evaporator system.

Advantageously, a system of aspects of the invention comprises a second distillation column (42). Advantageously, an inlet (94) of the second distillation column (42) is communicating with a first outlet (81) of the decanter (35). Advantageously, outlet (96) of second distillation column (42) is communicating with an inlet of the decanter (35).

Advantageously, as illustrated schematically in FIG. 2, a system of aspects of the invention comprises a third distillation column (43). Advantageously, an inlet (97) of the third distillation column (43) is communicating with a second outlet (82) of the decanter (35). Advantageously, outlet (99) of third distillation column (43) is communicating with an inlet of the decanter (35).

Advantageously, a system of aspects of the invention comprises a fourth distillation column (41). Advantageously, an inlet (91) of the fourth distillation column (41) is communicating with a second outlet (76) of the first distillation column (34).

It will be convenient to note that the steam stripper (36) and the first to fourth distillation columns (34, 41-43) have a top stream outlet provided with a condenser and a bottoms stream outlet provided with a heat exchanger, both provided with a return line to an inlet of, respectively, the steam stripper or distillation columns.

A system of aspects of the invention can further comprise a third (or fourth or more) fermentor. The third fermentor (not shown in FIGS. 1 to 3) can communicate with a first inlet (61) of the first fermentor (51).

According to another aspect of the invention, a system of the invention can be used for fermentative generation of products, advantageously solvents; advantageously n-butanol, acetone, or ethanol; 1,3-propanediol, n-butanol, or ethanol; or isopropanol, n-butanol, or ethanol; advantageously n-butanol, acetone, or ethanol; advantageously n-butanol.

Using a system of aspects of the present invention can generate substantially pure solvents, advantageously substantially pure n-butanol is formed. Advantageously, the obtained n-butanol has a purity comprised between 99.0% (w/w) and 99.9% (w/w), advantageously comprised between 99.5% (w/w) and 99.9% (w/w), advantageously between 99.7% (w/w) and 99.9% (w/w), advantageously a purity of 99.8% (w/w). Using a system of aspects of the present invention can generate substantially pure acetone as well.

EXAMPLES

Example 1

Integrated Multi-Stage Fermentation with Pervaporation Combined with Multi-Stage Condensation—Effect on Composition of Different Condensates The experimental set-up is schematically illustrated in FIG. 3.
Preparation of Culture Media Clostridium acetobutylicum strain ATCC 824 (Belgian coordinated collections of microorganisms, BCCM) was used in both fermentors. Freeze-dried cultures supplied in vacuum-sealed ampoules were used to inoculate prepared thioglycolate culture media (Oxoid Limited, Wesel, Germany). After inoculation and incubation at 37° C. for 72 h, 1.67 mL 80% glycerol solution was added per mL of culture. The culture was divided in 1.5 mL vials and subsequently stored as stock culture at −20° C. Anaerobic shake flasks containing 100 mL of a defined medium solution were inoculated with 0.1 mL of the glycerol stock culture and incubated at 35° C. for 28 h to obtain cultures in the mid-exponential phase (pH 4.5).

A concentrated mixture of 15% (w/w) C5/C6 carbohydrates mimicking a lignocellulosic hydrolyzate was used as feed for the fermentation. Glucose and xylose were used in a 2:1 ratio. The medium used for the seed culture and for the fermentations were identical. One liter of medium contains 0.01 g NaCl, 2.2 g ammonium acetate, 0.5 g $K_2HPO_4$, 0.5 g $KH_2PO_4$, 0.01 mg biotin, 3 mg p-aminobenzoic acid (PABA), 0.2 g $MgSO_4.7H_2O$, 0.01 g $MnSO_4.H_2O$, 11.1 mg $NH_4Fe$ citrate, 100 g glucose, 50 g xylose and 3 g yeast extract. The medium containing all components was prepared and filter-sterilized using a 0.2-µm Supor Membrane (VacuCap Filter, Pall Corporation, Port Washington, N.Y., USA).
Fermentor Setup with Pervaporation and Two-Stage Condensation A continuous two-stage ABE fermentation process was carried out, using a first fermentor (51) 3.4 L and a second fermentor (52) of 5.0 L. Both fermentors were supplied by Applikon Biotechnology (Schiedam, The Netherlands). The first fermentor and second fermentor were run at 32° C. The fermentors were sparged with nitrogen prior to inoculation with the seed cultures (10 vol %) until the dissolved oxygen tension was close to zero.

The in-house developed and assembled organophilic pervaporation unit (30) consisted of three rectangular flat membrane modules (Pervatech, Enter, the Netherlands) connected in series with a total membrane surface area of 0.027 m². The pervaporation unit is coupled to the first fermentor. An average permeate pressure of 20.0 mbar was established using a membrane vacuum pump (33) (SC920, KNF Neuberger GmbH, Freiburg, Germany). The membrane vacuum pump is arranged between a first condenser (31) and a second condenser (32), the first condenser being coupled to a permeate outlet of the pervaporation unit. The membrane vacuum pump is configured to maintain the first condenser (31) at a lower pressure than the second condenser. The first condenser (31) is made of glass, the second condenser (32) is made of (stainless) steel. The pH was monitored with a pH sensor InPro 3250 (Mettler-Toledo, Columbus, Ohio, USA) and left uncontrolled in both fermentors. The pH reached an average of 4.8 in the first and second fermentor over the entire course of the fermentation. The continuous fermentation process ran for 42 days.

A first condensation step is performed by partially condensing the permeate (21) at (about) 21 mbar. Referring to FIG. 3, the first condensate (25) exits the first condenser (31) as a bottoms stream. The remaining portion of permeate (21), residue stream (22), exits as the overhead stream from the first condenser (31). A second condensation step is then performed by condensing the residue stream (23) at (about) 1013 mbar forming a second condensate (27). The first and second condensation steps are performed at 2° C.

During the process, each day the content of acetone, ethanol and n-butanol obtained in the first and second condensates (25,27) was determined.
Analyses The determination of acetone, ethanol and n-butanol obtained in the first and second condensates (25,27) was performed by gas chromatography using an AT-WAX capillary column (60 m×0.32 mm; 1.00 µm film thickness) with flame ionization detection. The analysis was carried out under the following conditions: injector temperature 145° C., detector temperature 200° C., column temperature linearly ramping from 40 to 100° C. at 3° C. per min.; helium (carrier gas) flow rate, 1.6 mL min$^{-1}$; $H_2$ flow rate, 35 mL min$^{-1}$; air flow rate, 350 mL min$^{-1}$. D6-ethanol was used as an internal standard.

The results for the content of acetone, ethanol and n-butanol obtained in the first and second condensates (25,27) are presented in Table 1A for selected samples.

TABLE 1A

Content of acetone, ethanol and n-butanol obtained in the first and second condensates (25, 27).

| Sample name | Elapsed (day) | Acetone g/kg | n-butanol g/kg | Ethanol g/kg |
|---|---|---|---|---|
| PV1 (25) | 13 | 0.18 | 112 | 0.87 |
| PV1 (27) |  | 362 | 230 | 26 |
| PV2 (25) | 14 | 0.15 | 137 | 1 |
| PV2 (27) |  | 336 | 231 | 28 |
| PV3 (25) | 15 | 0.15 | 152 | 1 |
| PV3 (27) |  | 315 | 227 | 27 |
| PV4 (25) | 18 | 0.47 | 144 | 2 |
| PV4 (27) |  | 359 | 232 | 27 |
| PV5 (25) | 19 | 0.23 | 121 | 2 |
| PV5 (27) |  | 340 | 233 | 30 |
| PV6 (25) | 20 | 0.23 | 119 | 1 |
| PV6 (27) |  | 336 | 234 | 38 |
| PV7 (25) | 21 | 0.20 | 163 | 1 |
| PV7 (27) |  | 343 | 224 | 30 |

From the results, it can be seen that for each sample, the first condensate (25) is almost a pure solution of n-butanol and water, comprising only minor traces of ethanol and acetone, whereas the second condensate (27) is rich in acetone, n-butanol and ethanol.

After obtaining the first and second condensates (25,27), they can separately be introduced and purified in the further downstream processing to recover the produced solvents. Due to the different content of the formed condensates and their separate treatment, the energy consumption in the downstream processing can be decreased, compared to methods in the art only describing an improvement of the performance of the pervaporation step. In the present aspects, to the contrary, the energy consumption in the whole downstream processing after performing the pervaporation step is decreased, compared to the methods (and systems) described in the art. A method and system in aspects of the invention hence provide an overall improved energy efficiency and are thus more cost effective.

Similar results are obtained by condensing permeate (21) at 41 mbar in the first condensation step forming a first condensate (25), by condensing the residue stream (23) at 1013 mbar in the second condensation step forming a second condensate (27), and by performing the first and second condensation steps at 10° C. Results for the content of acetone, ethanol and n-butanol obtained in the first and second condensates (25,27), after running the continuous fermentation process for 335 hours, are presented in Table 1B. The average concentration of acetone, ethanol and n-butanol in the first product stream (18) (or feed) is also given.

TABLE 1B

Content of acetone, ethanol and n-butanol obtained in the first and second condensates (25, 27).

| condensate | acetone g/kg | n-butanol g/kg | ethanol g/kg | feed average concentration | | | |
| --- | --- | --- | --- | --- | --- | --- | --- |
| | | | | acetone g/kg | n-butanol g/kg | ethanol g/kg | total solvent g/kg |
| (25) | 2.86 | 74.58 | 1.98 | 1.61 | 6.75 | 0.90 | 9.26 |
| (27) | 187.51 | 275.10 | 26.00 | | | | |
| total | 40 | 114 | 7 | | | | |

Example 2

Simulation and Energy Calculation of Integrated Multi-Stage Fermentation with Pervaporation Combined with Multi-Stage Condensation—Effect on Energy Consumption Detailed simulations and energy calculations of a complete (conventional) process for production of acetone, n-butanol and ethanol are known for those skilled in the art and can be found in literature, for instance in Liu, J. et. al., Ind. Eng. Chem. Res. 48 (2009) 5551-5557.

In this example, a multi-stage fermentation according to aspects of the invention was simulated. More particularly, a continuous multi-stage fermentation integrated with organophilic pervaporation, coupled to a multi-stage condensation and followed by downstream processing was simulated. More particularly, the heteroazeotropic distillation process according to an embodiment of aspects of the present invention as illustrated in FIG. 2 was simulated using Chemcad 6.3.2 (Chemstations, Houston, Tex., USA) chemical process simulation software in which the NRTL (Non-Random Two Liquid model) thermodynamic model and a SODS (Simultaneous Correction Distillation System) type of column were chosen. The pervaporation process is modelled using Matlab R2010a software (The MathWorks, Natick, Mass., USA). Experimental values were used as input for the multistage condensation.

As comparative examples, the distillation process according to two conventional systems used for producing acetone, ethanol and n-butanol by fermentation was simulated as well. The corresponding prior art set-up is schematically illustrated in FIGS. 4 and 5.

The prior art system shown in FIG. 4 consists of a beer stripper with decanter and subsequent distillation columns, i.e. a continuous multi-stage fermentation with a conventional downstream processing. The fermentation in the prior art system shown in FIG. 4 is not coupled to pervaporation nor to a subsequent one-stage or multistage condensation. The prior art system shown in FIG. 5 uses pervaporation as in situ recovery technology, i.e. organophilic pervaporation is coupled to the second (51) of three subsequent fermentors followed by downstream processing. The pervaporation in the prior art system shown in FIG. 5 is not coupled to a multistage condensation. However, the pervaporation in FIG. 5 is, although not shown in the figure, coupled to a one-stage condensation. It is apparent for those skilled in the art that after performing the pervaporation in FIG. 5 a condensation follows to enable further downstream processing. In the setup of FIG. 5, a vacuum pump, although not shown either, is arranged after the (one and only) condenser. In FIGS. 4 and 5, a third fermentor (53) is communicating with an inlet of the first fermentor (51).

The energy consumption is calculated for a 100000 ton per annum n-butanol facility (operating 8400 hour per year and producing 11900 kg n-butanol per hour). The calculated energy consumption for an embodiment of aspects of the invention shown in FIG. 2 is compared with the energy consumption calculated for the prior art systems shown in FIGS. 4 and 5. Cooling and electricity costs were neglected in all cases. The energy required for feedstock preparation is not taken into account. In all cases, n-butanol is simulated to be obtained at a purity of 99.75% (w/w) and acetone at a purity of 99.03% (w/w), and ethanol is purified to 86.96% (w/w) with the remainder being acetone (2.65% (w/w)) and water (10.4% (w/w)). The solvent-depleted fermentation broth is concentrated in multiple effect evaporators to 20% of its original volume in all cases.

For the simulated process according to an embodiment of aspects of the present invention (FIG. 2), the design parameters for the different distillation towers are summarized in Table 2. The reboiler duty for the steam stripper and distillation columns, calculated using these design parameters, is given as well.

TABLE 2

Energy calculation for a simulated continuous multi-stage fermentation integrated with organophilic pervaporation coupled to multi-stage condensation and followed by downstream processing according to an embodiment of aspects of the present invention (FIG. 2).

|  | Steam stripper (36) | Distillation column (34) | Distillation column (41) | Distillation column (42) | Distillation column (43) |
| --- | --- | --- | --- | --- | --- |
| Diameter (m) | 2.6 | 2.4 | 1.5 | 3.0 | 2.6 |
| Number of trays | 20 | 30 | 30 | 17 | 10 |
| Number of columns | 2 | 1 | 1 | 1 | 1 |
| Reboiler duty (MJ/h) | 94249 | 31867 | 11318 | 47079 | 50000 |

Based on the calculated reboiler duty for the steam stripper and distillation columns, the total reboiler duty in this simulation scheme is 234513 MJ/h.

For the simulated process according to a prior art continuous multi-stage fermentation with a conventional downstream processing (FIG. 4), the design parameters for the different distillation towers are summarized in Table 3. The reboiler duty for the steam stripper and distillation columns, calculated using these design parameters, is given as well.

TABLE 3

Energy calculations for a simulated prior art continuous multi-stage fermentation with a conventional downstream processing (FIG. 4).

|  | Steam stripper (36) | Distillation column (34) | Distillation column (41) | Distillation column (42) | Distillation column (43) |
| --- | --- | --- | --- | --- | --- |
| Diameter (m) | 3 | 3.2 | 1.5 | 2.9 | 2.6 |
| Number of trays | 20 | 30 | 30 | 17 | 10 |
| Number of columns | 4 | 1 | 1 | 1 | 1 |
| Reboiler duty (MJ/h) | 237003 | 67001 | 11045 | 48335 | 50000 |

Based on the calculated reboiler duty for the steam stripper and distillation columns, the total reboiler duty in this simulation scheme is 413384 MJ/h. The Chemcad simulations mainly indicate an energy reduction in the steam stripper and the first distillation column (34) of an embodiment of aspects of the present invention (Table 2, FIG. 2), compared to the prior art fermentation with conventional downstream processing (cf. Table 3, FIG. 4).

For the simulated process according to a prior art continuous multi-stage fermentation integrated with organophilic pervaporation followed by conventional downstream processing (FIG. 5), the design parameters for the different distillation towers are summarized in Table 4. The reboiler duty for the steam stripper and distillation columns, calculated using these design parameters, is given as well.

TABLE 4

Energy calculations for a simulated prior art continuous multi-stage fermentation integrated with organophilic pervaporation followed by downstream processing (FIG. 5).

|  | Steam stripper (36) | Distillation column (34) | Distillation column (41) | Distillation column (42) | Distillation column (43) |
| --- | --- | --- | --- | --- | --- |
| Diameter (m) | 2.6 | 3.2 | 1.5 | 3.0 | 2.6 |
| Number of trays | 20 | 30 | 30 | 17 | 10 |
| Number of columns | 2 | 1 | 1 | 1 | 1 |
| Reboiler duty (MJ/h) | 94249 | 62683 | 10040 | 55223 | 50000 |

Based on the calculated reboiler duty for the steam stripper and distillation columns, the total reboiler duty in this simulation scheme is 272195 MJ/h. The Chemcad simulations mainly indicate an energy reduction in the first distillation column (34) of an embodiment of aspects of the present invention (Table 2, FIG. 2), compared to the prior art fermentation with pervaporation directly followed by downstream processing (cf. Table 4, FIG. 5).

Based on the calculated reboiler duties, the Chemcad simulations indicate an energy reduction in the distillation section of an embodiment of aspects of the present invention of 43% when compared to prior art fermentation with conventional downstream processing (cf. Table 3, FIG. 4), and of 14% when compared to prior art fermentation with pervaporation directly followed by downstream processing (cf. Table 4, FIG. 5). Hence, aspects of the present invention provide an improved energy efficiency compared with fermentation systems and methods described in the art.

The invention claimed is:

1. A method for producing solvents by fermentation, said method comprising the steps of:
   performing a first fermentation step by fermenting a feedstock in the presence of microorganisms forming a first product stream;
   performing a pervaporation step on the first product stream forming a permeate;
   performing a first condensation step by partially condensing the permeate forming a first condensate and a residue stream, wherein the first condensation step is performed at a first pressure being below atmospheric pressure;
   performing a second condensation step by condensing the residue stream at a second pressure higher than the first pressure forming a second condensate;
   distilling the second condensate to produce a stream enriched in a first range of solvents and a liquid stream depleted in the first range of solvents; and
   decanting the first condensate together with the liquid stream forming a phase enriched in a second range of solvents and an aqueous phase.

2. The method of claim 1, wherein the first condensation step is performed at a first pressure between 5 mbar and 200 mbar.

3. The method of claim 1, wherein the first and second condensation steps are performed at a same cooling temperature, the cooling temperature being between 0° C. and 20° C.

4. The method of claim 1, wherein an effluent from the first fermentation step is subjected to a second fermentation step forming a second product stream, the method further comprising introducing said second product stream in a steam stripper obtaining a top stream, wherein distilling the second condensate comprises distilling the top stream of the steam stripper together with the second condensate to produce the stream enriched in the first range of solvents and the liquid stream depleted in the first range of solvents.

5. The method claim 1, wherein the feedstock originates from sugar cane, corn mash, wheat or other carbohydrate containing feedstocks, or from biodiesel-derived glycerol.

6. The method claim 1, wherein the fermentation is performed in the presence of microorganisms of the *Clostridium* genus, or in the presence of genetically modified organisms derived thereof.

7. The method of claim 1, wherein the microorganism is *Clostridium acetobutylicum*, *Clostridium beijerinckii*, *Clostridium saccharobutylicum*, *Clostridium saccharoperbutylacetonicum*, or *Clostridium pasteurianum*.

8. The method of claim 1, wherein
the first condensate comprises a solvent rich phase comprising n-butanol and an aqueous phase comprising water;
the residue stream comprises acetone, n-butanol, ethanol, and water;
the first range of solvents in stream comprises acetone and ethanol;
the second range of solvents in the phase formed by decantation comprises n-butanol.

9. The method of claim 1, wherein:
the first fermentation step is performed by fermenting a feedstock in the presence of microorganisms of *Clostridium acetobutylicum;*
performing the first condensation step forms a first condensate comprising n-butanol and water, and a residue stream comprising acetone, n-butanol, ethanol, and water, the first condensation step is performed at a first pressure between 5 mbar and 200 mbar;
the first and second condensation steps are performed at the same cooling temperature, the temperature being between 0° C. and 20° C.;
the second condensate is distilled to produce the stream enriched in acetone and ethanol, and the liquid stream depleted in acetone and ethanol;
the first condensate is decanted together with the liquid stream forming a phase enriched in n-butanol and an aqueous phase.

10. The method of claim 1, wherein the phase enriched in the second range of solvents formed by decantation is purified by distillation, forming a first solvent.

11. The method of claim 1, wherein the stream enriched in the first range of solvents is purified by distillation, forming a stream enriched in a second solvent, and a stream enriched in a third solvent.

12. The method of claim 1, wherein:
the first fermentation step is performed by fermenting glycerol in the presence of microorganisms of *Clostridium pasteurianum* forming 1,3-propanediol remaining in the fermentation broth and a first product stream comprising n-butanol, ethanol, and water;
performing the first condensation step forms a first condensate comprising n-butanol and water, and a residue stream comprising n-butanol, ethanol, and water, the first condensation step is performed at a first pressure between 5 mbar and 200 mbar;
the first and second condensation steps are performed at the same cooling temperature, the temperature being between 0° C. and 20° C.;
the second condensate is distilled to produce a stream enriched in ethanol, and a liquid stream depleted in ethanol;
the first condensate is decanted together with the liquid stream forming a phase enriched in n-butanol and an aqueous phase.

13. The method of claim 1, wherein:
the first condensate comprises n-butanol and water;
the residue stream comprises isopropanol, n-butanol, ethanol, and water;
the first range of solvents in stream comprises isopropanol and ethanol;
the second range of solvents in the phase formed by decantation comprises n-butanol.

14. The method of claim 13, wherein:
the first fermentation step is performed by fermenting a feedstock, in the presence of microorganisms of *Clostridium acetobutylicum* or *Clostridium beijerinckii;*
performing the first condensation step forms a first condensate comprising n-butanol and water, and a residue stream comprising isopropanol, n-butanol, ethanol, and water, the first condensation step is performed at a first pressure between 5 mbar and 200 mbar;
the first and second condensation steps are performed at the same cooling temperature, the temperature being between 0° C. and 20° C.;
the second condensate is distilled to produce a stream enriched in isopropanol and ethanol, and a liquid stream depleted in isopropanol and ethanol;
the first condensate is decanted together with the liquid stream forming a phase enriched in n-butanol and an aqueous phase.

15. The method of claim 10, wherein the first solvent is n-butanol.

16. The method of claim 11, wherein the second solvent is acetone and the third solvent is ethanol.

17. The method of claim 1, wherein the liquid stream is obtained as a bottom stream from the distillation.

18. The method of claim 1, wherein the second condensation step produces a single stream comprising the second condensate.

* * * * *